US00PP25072P3

(12) United States Plant Patent
Lee

(10) Patent No.: US PP25,072 P3
(45) Date of Patent: Nov. 18, 2014

(54) ***RHODODENDRON* PLANT NAMED 'ROBLET'**

(50) Latin Name: ***Rhododendron* hybrid**
Varietal Denomination: ROBLET

(71) Applicant: Robert Edward Lee, Independence, LA (US)

(72) Inventor: Robert Edward Lee, Independence, LA (US)

(73) Assignee: PDSI, Loxley, AL (US)

( * ) Notice: Subject to any disclaimer, the term of this patent is extended or adjusted under 35 U.S.C. 154(b) by 0 days.

(21) Appl. No.: 13/694,810

(22) Filed: Jan. 7, 2013

(65) Prior Publication Data

US 2014/0196185 P1 Jul. 10, 2014

(51) Int. Cl.
*A01H 5/00* (2006.01)

(52) U.S. Cl.
USPC ..... Plt./238

(58) Field of Classification Search
USPC ..... Plt./239, 238
See application file for complete search history.

*Primary Examiner* — Anne Grunberg
(74) *Attorney, Agent, or Firm* — Cassandra Bright

(57) ABSTRACT

A new and distinct *Rhododendron* cultivar named 'ROBLET' is disclosed, characterized by distinctive coral colored semi double flowers with clear white margins. Plants are compact and bloom Spring, Summer and Fall. The new cultivar is a *Rhododendron*, suitable for ornamental garden purposes.

2 Drawing Sheets

Latin name of the genus and species: *Rhododendron* hybrid.

Variety denomination: 'ROBLET'.

BACKGROUND OF THE INVENTION

The new cultivar is a product of selection by the inventor. This new variety, hereinafter referred to as 'ROBLET', was discovered from a selection process involving two branch sports identified and selected by Robert Edward Lee Apr. 14, 2007 in Loxley, Ala., at a commercial nursery. The parent variety producing this naturally occurring mutation is *Rhododendron* 'Roblen' U.S. Plant Pat. No. 16,248, also invented by Robert Edward Lee. After identifying the two similar, but different branch mutations, the inventor confidentially evaluated and compared the two varieties over approximately two years. After confidential testing and evaluation, 'ROBLET' was selected by the inventor due to its more compact plant growth, better flower form and better foliage.

The inventor first directed propagation of 'ROBLET' by vegetative cuttings on Jun. 20, 2007 at a commercial nursery in Loxley, Ala. The inventor continued controlled testing and propagation, assessing stability of the unique characteristics of this variety. Multiple generations have been reproduced and have shown that the unique features of this cultivar are stable and reproduced true to type.

SUMMARY OF THE INVENTION

The cultivar 'ROBLET' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'ROBLET' These characteristics in combination distinguish 'ROBLET' as a new and distinct *Rhododendron* cultivar:

1. Spring, summer, and fall blooming.
2. Unique flower coloring of coral with a clear white margin.
3. Single to semi-double flowers.
4. Compact plant habit.
5. Good specimen plant.
6. Excellent performance in planters.
7. Very good foundation plant.
8. Does well as an understory plant in a woodland garden.
9. Hardy to Zone 7.
10. Attracts butterflies.

COMPARISON TO PARENT VARIETY

'ROBLET' is similar in most horticultural characteristics to the parent variety *Rhododendron* hybrid 'ROBLEN'. Plants of the new cultivar 'ROBLET' however, plants produce flowers that are distinctively coral with a white margin, whereas flowers of 'ROBLEN' are solid red. Additionally, the mature plant height and spread of the new variety are less than that of the parent variety. Plant habit is overall more compact in the new variety, compared to the parent.

COMMERCIAL COMPARISON

The inventor is not aware of any commercial varieties with semi double, coral and white colored flowers, with the unique re-blooming characteristics of 'ROBLET'.

BRIEF DESCRIPTION OF THE PHOTOGRAPHS

Figure 1:
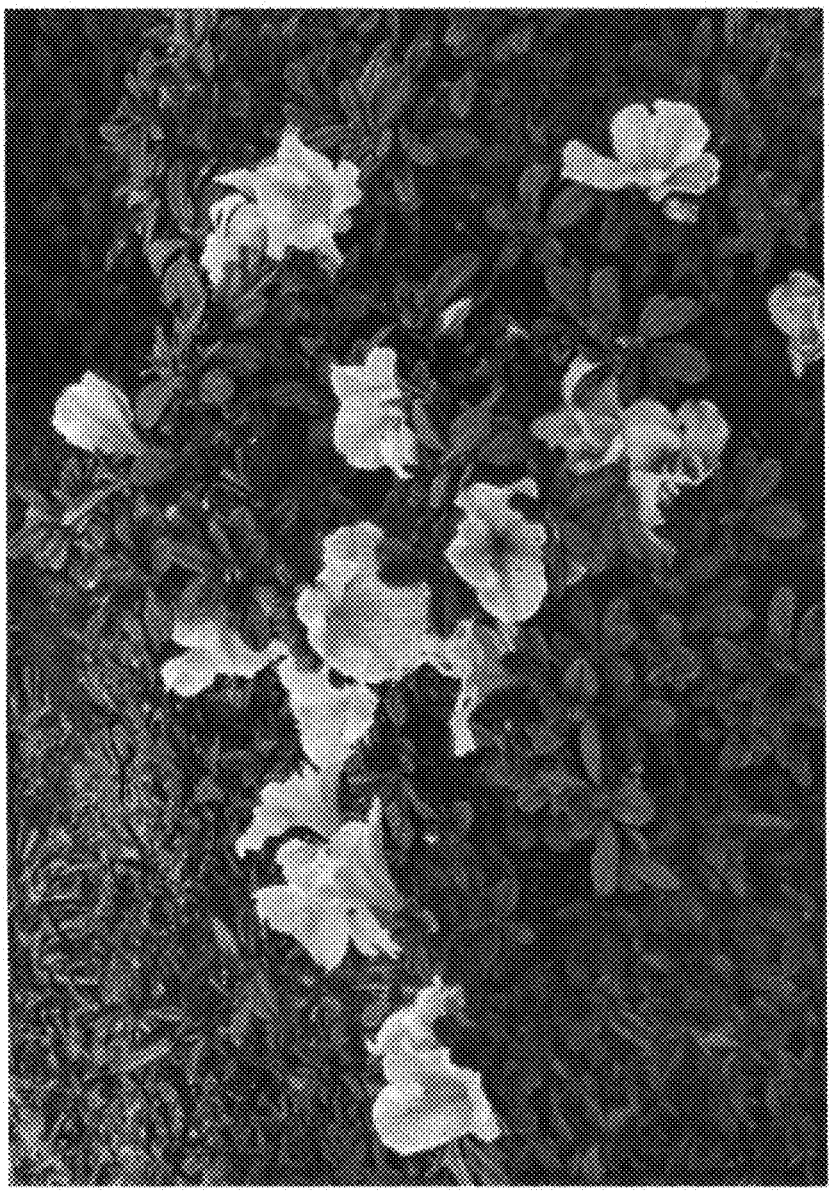

The accompanying photograph in FIG. 1 illustrates in full color a typical plant of 'ROBLET' grown outdoors in Alabama. The plant is approximately 2 years old, and is shown growing in the ground.

Figure 2:
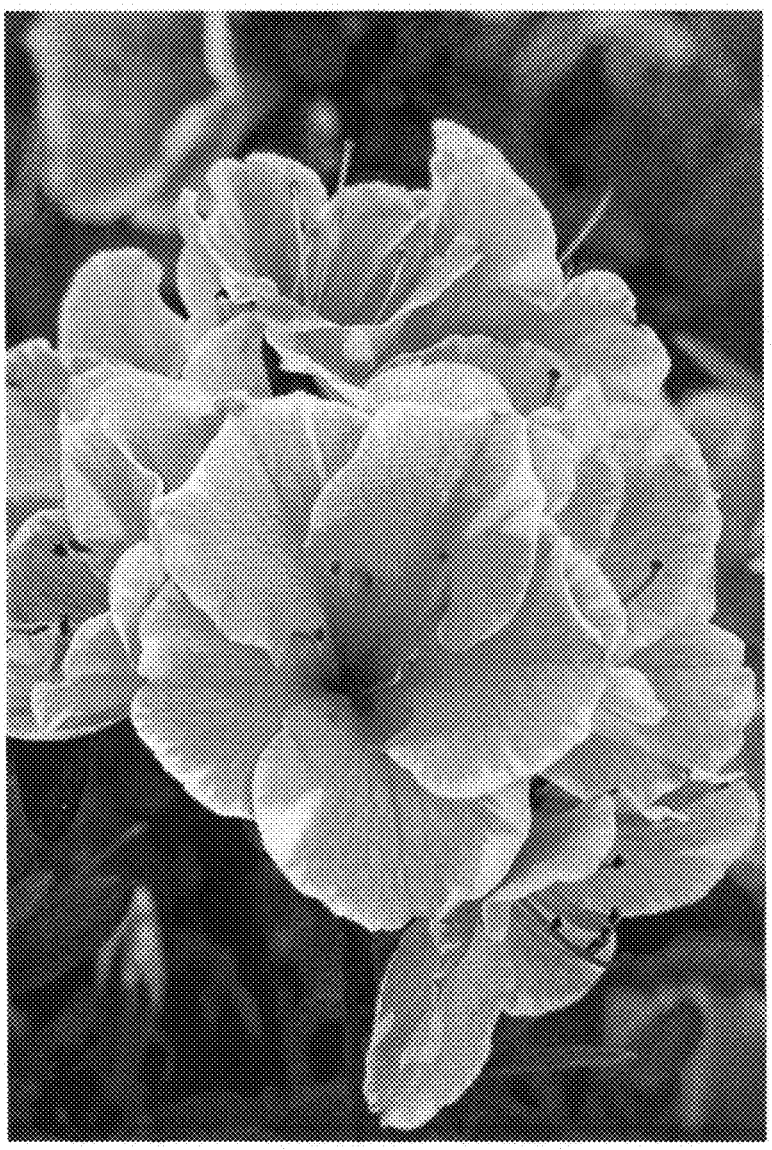

FIG. 2 illustrates in full color a close up of typical flowers of 'ROBLET'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001 except where general terms of ordinary dictionary significance are used. The following observations and measurements describe 'ROBLET' plants grown outdoors in Loxley, Ala. Plants are approximately 2 years old, in a 3 gallon nursery container. Measurements and numerical values represent averages of typical plant types.

Botanical classification: *Rhododendron* hybrid 'ROBLET'.

PROPAGATION

Typically by semi-hardwood cuttings in Spring and Summer.

PLANT

Growth habit: Compact evergreen shrub. Slow to moderate growth rate.

Height: Approximately 35 cm to top of foliar and flowering plane.

Plant spread: Approximately 70 cm.

Branching characteristics: Well branched, approximately 20 primary branches from center of plant, angled approximately 75° from center of plant. Each primary branches has 4 to 10 lateral branches.

Primary branches:

- *Length of primary branches*.—Approximately 18 to 28 cm.
- *Diameter of primary branches*.—Approximately 0.8 cm.
- *Primary branch strength*.—Very strong, difficult to break.
- *Primary branch color*.—Near RHS Yellow-Green N144D, with age, becoming covered with a thin bark like layer colored near Brown 200C.
- *Primary branch texture*.—Young growth covered in appressed hairs, approximately 0.15 cm long, colored near Brown 200B. Older growth scaly, covered in appressed hairs colored near White 155D.

Lateral branches:

- *Number of lateral branches*.—Approximately 8 to 20 per primary branch.
- *Length of lateral branches*.—Approximately 3 to 7 cm.
- *Diameter of lateral branches*.—Average 0.35 cm.
- *Lateral branch strength*.—Very strong, flexible.
- *Lateral branch color*.—Near RHS Yellow-Green 144C.
- *Lateral branch texture*.—Covered in moderately dense appressed hairs, colored near RHS Brown 200B.

Internode length: Range between 1.5 to 3.5 cm.

Age of plant described: Approximately 2 years.

FOLIAGE

Leaf:

- *Type*.—Simple.
- *Arrangement*.—Alternate.
- *Average length*.—Approximately 3.5 cm.
- *Average width*.—Approximately 1.6 cm.
- *Shape of blade*.—Narrow spatulate to obovate. Apex broader, more spatulate on older foliage.
- *Apex*.—Rounded, with a very shallow/short mucronate tip.
- *Base*.—Broad attenuate.
- *Attachment*.—Stalked.
- *Margin*.—Entire.
- *Texture of top surface*.—Leathery, slightly pubescent. Hairs less than 1 mm.
- *Texture of bottom surface*.—Glabrous, matte.
- *Foliage scent*.—None.
- *Color*.—Young foliage upper side: Near RHS Green 137B. Young foliage under side: Near RHS Yellow-Green 144B. Mature foliage upper side: Near RHS Green 137A, but darker. Mature foliage under side: Near RHS Green 138B.
- *Venation*.—Type: Pinnate. Venation color upper side: Near RHS Yellow-Green 144B. Venation color under side: Near RHS Yellow-Green 144C.
- *Petiole*.—Length: About 1.2 cm. Diameter: About 0.3 cm. Color: Near RHS Yellow-Green 144D, upper and lower surfaces.

FLOWER

Bloom period: Plants begin flowering, around late March, and continue to produce flowers throughout Summer and Fall. Flowering ends with frost, typically October or November.

Flower:

- *Arrangement*.—Single or semi double, perfect, open funnel shaped.

Peduncle:

- *Length*.—Average 1.3 cm.
- *Diameter*.—0.3 cm.
- *Color*.—Near RHS Yellow-Green 145C, very faintly flushed with Red 48C close to flower.
- *Texture*.—Densely pubescent.
- *Aspect*.—Straight to very slightly curved. Angle of attachment, approximately 45° angle from stem.

Flowers:

- *Length*.—Average 5.0 cm.
- *Diameter*.—Average 6.5 cm.
- *Facing direction*.—Outwardly and upwardly facing.
- *Persistent or self-cleaning*.—Petals self cleaning.
- *Fragrance*.—Very faint.

Tube:

- *Tube length*.—Approximately 2.0 cm.
- *Tube width a widest point*.—Approximately 2.2 cm.
- *Tube width and narrowest point*.—Approximately 0.9 cm.

Petals:

- *Unfused petal segments*.—Length: Approximately 2.5 cm. Width: Approximately 3.0 cm.
- *Apex*.—Retuse.
- *Shape of petal*.—Unfused portion, obovate.
- *Petal margin*.—Entire to infrequent crenations. Ruffled aspect along margin.
- *Petal arrangement*.—Approximately ⅓ fused from base.
- *Petal number*.—5.
- *Petal texture*.—Smooth.
- *Color*.—Upper surface at first opening: Near Red 53D. Under surface at first opening: Near RHS Red52A. Inner surface at maturity: Near RHS Red 50C, veins darker, near Red 53D. Margins White N155C. Irregular small dots near Red-Purple 61B occasionally occur at the widest point in the throat. Outer surface at maturity: Near RHS Red 48D, veins darker, near Red 52A. Margin blotches near White N155C. Upper surface at fading: Near RHS Red 55C, veins darker, near Red 54B. Margins White N155C. Irregular small dots near Red-Purple 61B occasionally occur at the widest point in the throat. Under surface at fading: Near RHS Red 49A, veins darker, near Red 52B. Margin blotches near White N155C.

Bud:

*Shape*.—Elliptic.

*Length*.—3 cm.

*Diameter*.—1.5 cm.

*Color*.—Near RHS Red 49A, blotched White N155C.

Calyx/sepals:

*Quantity per flower*.—5 sepals.

*Shape*.—Narrow deltate.

*Length*.—0.5 cm.

*Width*.—0.3 cm.

*Apex*.—Acute.

*Base*.—Fused.

*Margin*.—Entire.

*Texture*.—Highly pubescent. Color: Inner Surface: Near RHS Yellow-Green 145A. Outer Surface: Near RHS Yellow-Green 145B.

REPRODUCTIVE ORGANS

Stamens:

*Number*.—5.

*Length*.—4.0 cm.

*Width*.—0.1 cm.

*Color*.—Near RHS Red 49C.

*Anthers*.—Length: Approximately 0.3 cm. Color: Near RHS Greyed-Orange 166B. Pollen: Not observed to date.

Pistil:

*Number*.—1.

*Length*.—5 cm.

*Style*.—Length: 4.8 cm. Color: Near RHS Red-Purple 58B.

*Stigma*.—Globular, colored near Red-Purple 59A.

*Ovary*.—Sericeous texture. Approximately 0.2 cm in diameter. Colored near Yellow-Green 147A. Hairs colored near White N155D.

OTHER CHARACTERISTICS

Disease and pest resistance: Not observed to be susceptible nor resistant to normal diseases and pests of *Rhododendron*.

Temperature tolerance: USDA Zone 7.

Fruit/seed production: Not observed to date.

What is claimed is:

1. A new and distinct cultivar of *Rhododendron* plant named 'ROBLET' as herein illustrated and described.

* * * * *